(12) United States Patent
Jarvies et al.

(10) Patent No.: US 7,491,339 B2
(45) Date of Patent: Feb. 17, 2009

(54) APPARATUS AND METHOD FOR TREATMENT OF CHEMICAL AND BIOLOGICAL HAZARDS

(75) Inventors: Iain Fraser Jarvies, Aberdeenshire (GB); Steve Barfield, Aberdeenshire (GB)

(73) Assignee: Albagaia Limited, Strichen (GB)

( * ) Notice: Subject to any disclaimer, the term of this patent is extended or adjusted under 35 U.S.C. 154(b) by 411 days.

(21) Appl. No.: 10/523,497

(22) PCT Filed: Aug. 6, 2003

(86) PCT No.: PCT/GB03/03431

§ 371 (c)(1),
(2), (4) Date: Feb. 4, 2005

(87) PCT Pub. No.: WO2004/014437

PCT Pub. Date: Feb. 19, 2004

(65) Prior Publication Data

US 2005/0269272 A1    Dec. 8, 2005

(30) Foreign Application Priority Data

Aug. 7, 2002    (GB) ................. 0218314.3

(51) Int. Cl.
*B01D 17/00* (2006.01)
(52) U.S. Cl. ................. 210/748; 204/193; 204/157.15; 422/186; 422/20
(58) Field of Classification Search ......... 210/748, 210/739; 204/193, 157.15; 422/20, 186.3
See application file for complete search history.

(56) References Cited

U.S. PATENT DOCUMENTS

| | | | |
|---|---|---|---|
| 4,039,431 A | | 8/1977 | Baillie |
| 4,448,750 A | * | 5/1984 | Fuesting ..................... 422/20 |
| 5,116,582 A | * | 5/1992 | Cooper et al. ............. 422/186.3 |
| 5,130,031 A | * | 7/1992 | Johnston ..................... 210/748 |
| 5,174,877 A | * | 12/1992 | Cooper et al. ............... 204/193 |
| 5,395,522 A | * | 3/1995 | Melanson et al. ........... 210/202 |
| 5,449,466 A | * | 9/1995 | Peebles et al. .............. 210/747 |
| 6,555,011 B1 | * | 4/2003 | Tribelsky et al. ............ 210/748 |

FOREIGN PATENT DOCUMENTS

| | | |
|---|---|---|
| EP | 0105814 | 4/1984 |
| GB | 2165155 | 4/1986 |
| GB | 2252707 | 8/1992 |
| GB | 2309876 | 8/1997 |
| GB | 2332350 | 6/1999 |
| JP | 05305125 A | 11/1993 |
| JP | 09253637 A | 9/1997 |
| WO | WO 92/19284 | 11/1992 |
| WO | WO 99/10273 | 3/1999 |
| WO | WO 9961075 A | 12/1999 |

* cited by examiner

*Primary Examiner*—Walter D Griffin
*Assistant Examiner*—Cameron J Allen
(74) *Attorney, Agent, or Firm*—Drinker Biddle & Reath LLP

(57) ABSTRACT

The present invention relates to a method for the deactivation and/or destruction of hazardous materials such as chemical or biological agents. The invention further relates to apparatus for treating hazardous material and for decontaminating items that may have come into contact with it, the apparatus comprising a treatment vessel or chamber and a light source capable of irradiating a catalyst within the treatment vessel or chamber with a predetermined wavelength of light.

5 Claims, 4 Drawing Sheets

APPARATUS AND METHOD FOR TREATMENT OF CHEMICAL AND BIOLOGICAL HAZARDS

The present invention relates to an apparatus for the treatment of hazardous materials specifically prions, chemical and biological agents. The invention further relates to a method for using such an apparatus.

DESCRIPTION OF THE RELATED ART

The risks associated with contamination caused by chemical and biological agents of various kinds are well known. Medical equipment and surgical instruments are required to be sterilised to eliminate a growing range of infectious agents including more recently prions implicated in new variant Creusfeld Jacob Disease (nvCJD). Proteins exhibit huge variation in structure. However, they are formed in similar ways and thus display certain structural elements and characteristics that are common. The primary structure of proteins is determined by the amino acid sequence and pendant side groups. The amino acid chains are then folded to form various secondary structures designated as α-helices or β-sheets. Secondary structure is determined by the folding of the amino acid chains and interactions between the various side groups. Further associations may also form, depending on the protein's environment. For example different hydrophilic and hydrophobic groups or areas within the protein molecule are sensitive to the medium in which the molecule may be suspended. The prion protein plays an essential role in the pathogenesis of a group of sporadic, genetically determined and infectious fatal degenerative diseases, referred to as prion diseases, or transmissible encephalopathys (TSE's), affecting the central nervous system of humans and other mammals. The cellular prion protein is encoded with a single copy gene, highly conserved across mammalian species. In prion diseases this protein undergoes conformational changes involving a shift from α-helices to β-sheet structure. The structures of the proteins, both native and rogue, have been extensively investigated. The one of most interest and immediate impact to humans is the protein associated with nvCJD. What is unusual about the protein that is associated with TSEs is the extreme robustness it exhibits. This is thought to be due its β-sheet-sheet structure. Prions are known to survive temperatures in excess of 300° C. Such proteins thus represent present particular problems in terms of their transmission and destruction. The nvCJD prion is known to have a high affinity for stainless steel and other metals posing significant difficulties for the sterilisation of medical equipment, such as surgical instruments. At the same time, considering hazards unrelated to the medical field, chemical and biological agents, such as those used as weapon materials, pose significant handling and disposal risks.

For the purposes of the present application, the term "hazardous material" means any organic material that may be inimical to human well being and as such may be classed as a chemical or biological hazard. "Hazardous material" includes, but is not restricted to, viral material, bacterial material, prions, proteins, lipids, chemical and biological agents/material with associated organophosphate bases, organic waste or by-products associated with pharmaceutical processes and blood products, and further includes all of said agents in isolation and when found within, on the surface of or bonded to other material, instruments or equipment. The term "target material" is used throughout in reference to a "hazardous material" which is to be treated according to the method of the invention.

The term "treatment" is used in its broadest form and encompasses the deactivation and destruction of hazardous material. Relatively minor modifications to the structure or conformation of a particular agent may be sufficient to render it inactive without the need for the agent to be destroyed or decomposed into constituent elements.

While some methods for treating such agents are known, these typically involve the use of reagents which are themselves difficult to handle and which have associated safety issues. Fluorine and ozone for example may be effective in catalysing such processes, but create significant handling problems and are not suited to use in an open bath apparatus. Furthermore some prior art processes are required to be carried out at very high temperatures and/or pressures. The apparatus used in such processes is necessarily complex and expensive in light of the associated handling difficulties.

There remains therefore a need for a method for the deactivation or destruction of prions, chemical and biological agents, which is effective, efficient and broadly applicable. There is a particular need for an apparatus and a treatment method that can be used to sterilise or decontaminate equipment and instruments that may have come into contact with hazardous material. The present invention as set out below provides such an apparatus and a method for its use.

BRIEF SUMMARY OF THE INVENTION

Accordingly, in a first aspect the present invention provides apparatus for treating hazardous material and for decontaminating items that may have come into contact with such material. In its broadest form such apparatus comprises an operator accessible treatment vessel or chamber and a light source capable of irradiating a catalyst within the treatment vessel or chamber with a predetermined wavelength.

A first embodiment of the invention provides an apparatus, for batch treatment of hazardous material, comprising a treatment vessel for holding material to be treated; a light source for irradiating the contents of the treatment vessel; circulation or agitation means and progress and/or by-product monitoring means. The treatment vessel may comprise a 'glove box' type lid facilitating manipulation of the bath contents by an operator. An automatic light source cut-off may be incorporated in order to enhance operator safety.

A second embodiment provides an apparatus comprising a treatment vessel having one or more decontamination trays for holding hazardous material or items to be treated, a light source for irradiating the contents of the treatment vessel, medium distribution means for circulating a carrier medium within and/or through the apparatus and by-product monitoring means.

A third embodiment provides an apparatus comprising a holding tank for holding a carrier medium; a catalyst hopper for holding a catalyst; a mixing vessel for mixing the carrier medium and the catalyst; one or more treatment chambers each having a housing which contains a plurality of treatment beds and a light source; and a distribution header for controlling the flow of carrier medium and catalyst into the treatment chambers. Preferably, each treatment bed comprises means for inducing turbulent flow within the carrier medium flowing therein.

A second aspect of the present invention provides a method for the deactivation and/or destruction of hazardous material comprising the step of irradiating the hazardous material in the presence of a catalyst with light having a wavelength in the range of 310 nm to 400 nm. The method of the invention causes sufficient chemical modification of the hazardous material so as to deactivate or destroy it.

Preferably, the catalyst is $TiO_2$ in either rutile or anatase form and preferably the method is carried out at ambient temperature (of between about 15 to 35° C.) and pressure (of between about 1 to 5 bar).

The method may be carried out in any water based carrier medium that is compatible with the target material and catalyst. Preferably the carrier medium is water. Judicious choice of treatment medium is required in order to ensure reliable and effective treatment. In particular when considering the treatment of objects or instruments contaminated with prions for example the physical characteristics of the apparatus and method should facilitate a suitable reaction interface. This involves consideration of the composition and viscosity of the carrier medium and the path-length of the apparatus such that the target material, catalyst and photons from the light source are brought together in a manner suitable to effect treatment. It follows that a medium that is relatively low in viscosity and has appropriate optical characteristics (over the wavelength(s) of the light source) is desirable. In other words, the viscosity must be such as to allow the bringing together of the target material and the catalyst and the configuration of the apparatus and the optical characteristics of the medium must allow sufficient transmission of light to the target/catalyst reaction site.

Thus, the present invention provides for the treatment hazardous material such as prions linked with human or animal nvCJD in both a$\alpha$ and $\beta$ forms and for treatment of instruments and equipment that may have been contaminated with said material. The method, and apparatus for implementing it, are also applicable to the destruction of chemical agent material, typically organophosphate based systems, as typified by VX or Sarin, but additionally blistering and choking agents as typified by Mustard Gas and Tear Gas. Depending upon the conditions employed, the invention provides for total destruction of some hazardous material by breaking it down into its constituent parts, principally carbon dioxide, nitrogen, water and inorganic salts, or alternatively provides for sufficient modification of target materials so as to render them inactive. The invention can also deactivate or destroy many other biohazards, viral and bacteriological material, and many commonly industrially produced organic materials. Furthermore, the method of the invention can be employed to decontaminate materials, equipment, instruments and the like which may have come into contact with hazardous material.

The method of the invention represents an efficient means of deactivating and/or destroying of hazardous material under mild conditions on a batch basis. Further advantages of the invention are described below.

BRIEF DESCRIPTION OF THE DRAWINGS

The various aspects of the invention are described in detail below with reference to the accompanying drawings in which.

DETAILED DESCRIPTION OF THE INVENTION

Figure 1:
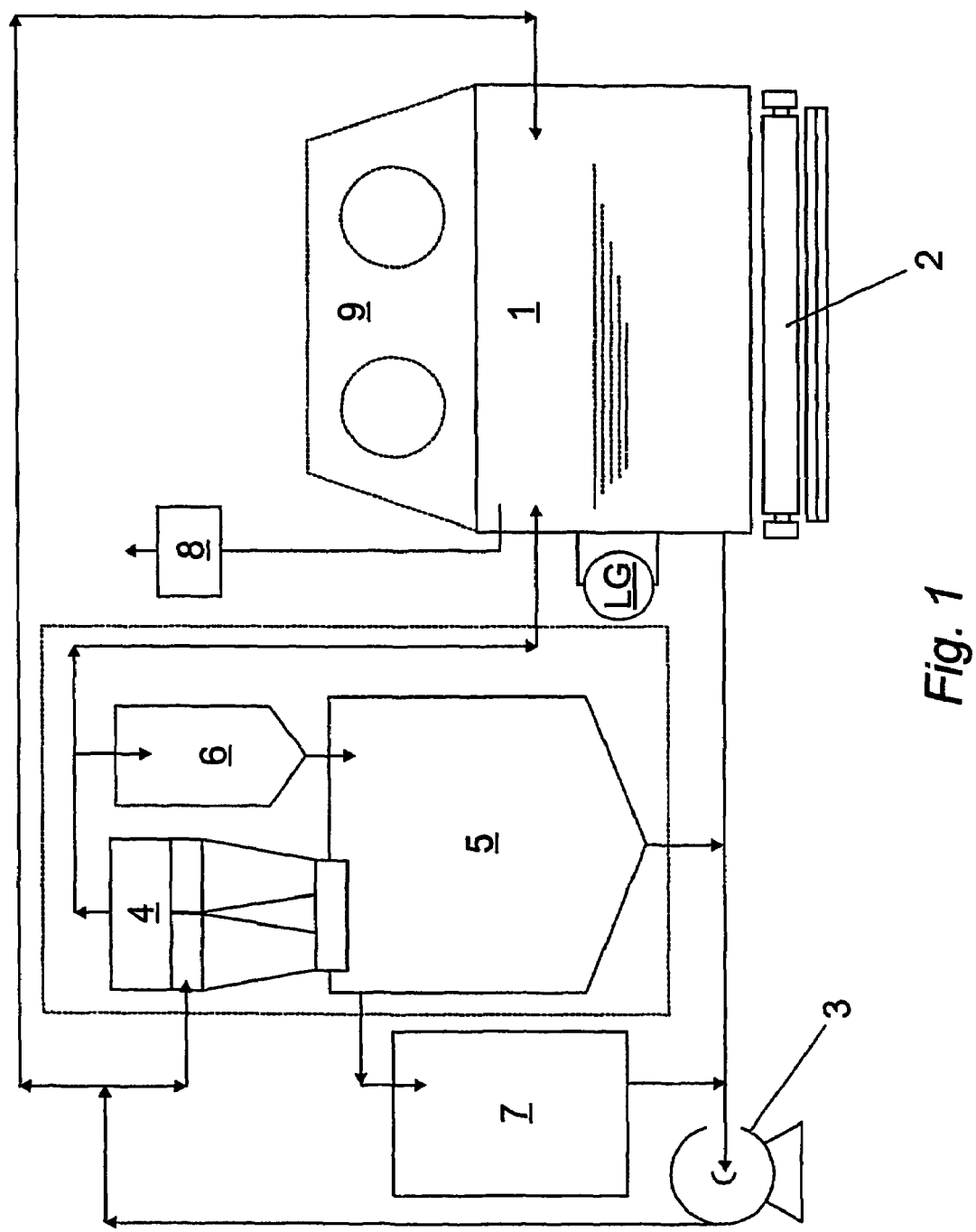
FIG. 1 shows a first embodiment of an apparatus according to the invention.

In the drawings similar reference numerals have been used to designate components common to each of the alternative embodiments.

In its broadest form the invention provides a decontamination method for the treatment of hazardous material comprising the step of irradiating the hazardous material in the presence of a catalyst, with light of a suitable wavelength, to deactivate or destroy the target material through photocatalytic oxidative processes. In general terms, the apparatus of the present invention comprises (i) a treatment chamber in which the catalyst and the target material may be irradiated with light of a suitable wavelength (and energy) and (ii) a light source capable of producing the desired wavelength. The light source wavelength and intensity may be adjusted to optimise the process depending upon the nature of the target material and the choice of catalyst. A liquid carrier, preferably a water based medium, is used to introduce hazardous material into the treatment chamber for irradiation.

Without being bound by theory, the invention is considered to be the result of an interaction of light energy (photons), the catalyst and water elements that forms hydroxyl radicals which cleave sections of, or links in, molecules of the target material ('primary effects'). The action of UV light contributes directly to the breakdown of target materials through photolysis of molecules present. In conjunction with the formation of hydroxyl radicals hydrogen peroxide ($H_2O_2$) is also produced. This oxidising agent assists and speeds the decontamination process cycle. The primary effects of hydroxyl radicals allow secondary processes (such as attack by $H_2O_2$) to act upon vulnerable parts of the molecules. The ultimate result is the break down of hazardous material into simple (safe) moieties, formation of inorganic salts within the carrier medium and production of off-gases, such as $CO_2$.

The method of the invention employing highly reactive hydroxyl radicals and $H_2O_2$ produced through irradiation of a suitable catalyst can be utilised to oxidise prion proteins decomposing them to $NO_x$, $CO_2$, water and various inorganic salts. Attack on a prion protein molecule by a hydroxyl radical causes selective breakage of multiple bond linkages, thus permanently altering the crucial relationship between amino acid units and inducing changes to their proper attachment and alignment to each other (and to associated components such as carbohydrates and possibly lipids). This effect changes the spatial configuration of the prion protein impacting upon its ability to reproduce properly. It is possible that even small alterations in the protein composition and/or configuration are sufficient to impede biological activity of a prion molecule. Any alteration in the structural make-up and configuration reduces the resistance of the prion to further oxidative processes, such as attack by $H_2O_2$, thus increasing the rate of complete oxidation of the molecule.

Contact between the hydroxyl radical/hydrogen peroxide production interface and the target material on the equipment/instruments or the like, using the water based carrier medium with the catalyst, is maximised. This may be addressed by ensuring that the catalyst within the water carrier is migrated to the interface using suitable circulation or entraining processes. Minimising the spatial offset in this manner increases the effects of the short-lived radicals produced upon irradiation. Spatial offset distance is further aided through the use of small catalytic particulate (3-5 microns).

Prior cleaning of gross material make take place within the decontamination train, that minimises the volume of material to be decontaminated, and improves throughput.

Increasing the intensity of irradiation and/or increasing the surface area of catalyst irradiated can increase radical production. Additional catalyst may be introduced to speed the process and replace catalyst extracted from the waste stream.

The catalyst may be any photosensitive material, which allows, through illumination with light of a suitable wavelength, a reaction with the associated hazardous material to occur. Suitable catalyst materials include for example $TiO_2$, $TiO_3$, ZnO, CdS, CdSe, $SnO_2$, $WO_3$, $Fe_2O_3$ and $Ta_2O_5$. An example of a preferred catalyst is $TiO_2$. Irradiation of the catalyst produces active sites (on what is in effect a semiconductor surface) causing water absorbed to the surface to be oxidised. Highly reactive hydroxyl radicals formed in this manner react with (and ultimately decompose) the target material present in the system.

The catalyst may be used in any form that provides suitable contact with the target material. For example, the catalyst may be dispersed in the carrier medium or it may be coated onto or mixed with the various materials to be decontaminated or destroyed. A catalyst module such as a column or tower coated with catalyst material may be employed. Alternatively, the catalyst may be coated onto internal surfaces of the apparatus, enhancing robustness and self-cleaning capability. Recovery of the catalytic material for reuse, increasing efficiency of the process, may be provided for as described below.

While light in the range of 310 nm to 400 nm is preferred, the wavelength of light employed may vary depending upon the catalyst used, the medium used and the nature of the target material. The wavelength to be used may be selected based on the absorption characteristics of the target material, thus increasing efficiency. As photo-generated hydroxyl radicals are the primary agents responsible for the decontamination/destruction processes various parameters may be changed to optimise the effect upon any given target material. The selected wavelength may be produced for example using a standard mercury lamp in conjunction with a suitable filter.

The method of the invention degrades target materials ultimately reducing them to simple reaction products such as $CO_2$. The evolution of $CO_2$ or any other reaction product can thus be used to monitor the degree and rate of the process. Suitably off-gas production or target material break down may be monitored using techniques such as Raman spectroscopy, mass spectrometry, in vitro tests or other known techniques appropriate to any particular hazardous material.

Characteristics of the method of the invention are detailed in Table 1, together with comparable data for various prior art methods. The 'efficiency' values indicate the rate and effectiveness of electron transfer during the treatment process.

TABLE 1

| Catalyst | Efficiency (eV) | Medium | Output toxicity | Temp (° C.) | Pressure (bar) | Power |
|---|---|---|---|---|---|---|
| $TiO_2$ (present invention) | 3.34 | Water | Very low | <36 | <10 | Low |
| Ag (II)* | 1.98 | Nitric acid | High | ~90 | 10 | High |
| Ruthenium* | 1.8 | $H_2SO_4$ | High | ~90 | 10 | High |
| Chlorination* | 1.3 | Water | High | ~40 | <10 | Low |
| $H_2O_2$** | 2.00 | Water | Low | <36 | <10 | Low |

*Indicates prior art process;
**Hydrogen peroxide not a catalyst as such - included for comparison purposes only.

Prior art methods (other than those detailed in Table 1) include hydrogenation and methods employing molten metals or supercritical water. These additional methods all pose significant hazards themselves due to the operating conditions required in order to be effective (for example, all three require temperatures in excess of 600° C.; and hydrogenation and supercritical water methods operate at pressures of about, or in excess of, 100 bar). Treatment with fluorine, possibly the strongest oxidising agent known, is also effective, but extremely difficult and dangerous to handle.

The method of the invention provides an effective and efficient process for the deactivation and/or destruction of hazardous material, on batch or continuous basis, while overcoming the shortcomings of some prior art methods in terms of operational requirements and characteristics. The present invention facilitates decontamination treatments to be carried out under ambient temperature and pressure conditions through a method and apparatus which has minimal moving parts, is easy to maintain and operate and which is readily scalable.

TABLE 2

| Class of Compound | Examples |
|---|---|
| Alkanes | Methane; pentane; heptane; n-dodecane; cyclohexane, paraffin |
| Haloalkanes | mono-, di-, tri-, and tetrachloromethane; dichloropropane Pentachloroethane; di and tribromoethane; 1,2-dichloropropane |
| Aliphatic Alcohols | methanol; ethanol; n- and iso-propanol; butanol; penta-1, 4-diol |
| Aliphatic Carboxylic Acids | methanoic, ethanoic; trichloroacetic; butyric; oxalic |
| Alkenes | propene; cyclohexene |
| Haloalkenes | di-, tri- and tetra-chloroethene; hexafluoropropene |
| Aromatics | benzene; naphthalene, Tributyl Phosphate |
| Haloaromatics | chloro and bromobenzene; chlorobenzenes; halophenols |
| Phenols | phenol; hydroquinone; catecol; resorcinol; cresol, nitrophenol |
| Aromatic Carboxylic Acids | benzoic; phthalic; salicyclic |
| Polymers | polyethylene; PVC |
| Surfactants | polyethylene glycol; p-nonyl phenyl ether; sodium dodecyl benzene sulphonate; paraxon; malathion |
| Herbicides | methyl viologen; atrazine; simazine; bentazon |
| Pesticides | DDT; parathion; lindane, monocrotophos |
| Dyes | methylene blue; rhodamine B; methyl orange; fluorescein |
| Explosives | Trinitrotoluene |
| Cyanotoxins | Microcystins, Anatoxin-a |
| Bacteria Proteins | E. Coli., Serratia marcescens, |

Table 2 lists compounds successfully destroyed using the present invention. Tributyl phosphate, appearing in the 'Aromatics' class, is a simulant for nerve agents.

TABLE 3

| Material | Concentration (% v/v) | Wavelength (nm) | Time (min) | Efficiency (%) |
|---|---|---|---|---|
| Methanol | 0.1 | 385 +/− 10 | 20 | 99.5 |
| Paraffin | 0.1 | 385 +/− 10 | 40 | 99.75 |
| Benzene | 0.1 | 380 +/− 10 | 60 | 99.9 |

Table 3 details a number of test materials and the conditions under which they were treated. In each case treatment was carried out at atmospheric pressure and at room temperature. The treatment efficiency (which in the case of the three test materials corresponds to destruction of the compounds in question) was measured using spectrophotometric techniques.

The specific embodiments of an apparatus according to the invention described below may each be provided with a circulation system, a catalyst feed mechanism, and a catalyst recovery system. In addition there may be a flushing mechanism to remove excess free catalyst deposits from the cleaned instruments or tools and materials prior to final removal and drying. Larger units having the same basic unit structure may be complemented by material towers coated with the catalyst through which the contaminated material in the water-based matrix is allowed to percolate, thus increasing exposure of the contaminants to the catalyst and UV sources.

Prior cleaning of gross material make take place within the decontamination train, that minimises the volume of material to be decontaminated, and improves throughput.

A first embodiment of an apparatus according to the invention is shown schematically in FIG. 1. The apparatus comprises a treatment chamber or bath (1), a light source (2), a circulation pump (3), an off-gas monitor/treatment unit (8), a catalyst recovery system (4) and a holding tank (5). A catalyst hopper (6) and a medium storage unit (7) for storing the catalyst and carrier medium prior to use are also provided. This first embodiment has been designed for small quantity throughput of, for example, surgical instruments for decontamination or for destruction of small quantities of target material. Manual manipulation of items in the treatment chamber may be facilitated through use of a glove-box type lid (9). This apparatus is designed for operation by medical staff in for example medical or dental practices.

Catalyst material and carrier medium are introduced into the holding tank (5), from the catalyst hopper (6) and the medium storage unit (7) respectively, and from there into the treatment chamber (1). The catalyst is typically suspended in the carrier medium and suitable stirring means may be provided in order to ensure that suspension is maintained and that the suspension circulates within the chamber (1). The contaminated equipment or target material (not shown) is placed in to the bath; the lid closed and interlocks (not shown) engaged before the process commences. In order to maintain the catalyst in suspension within the carrier medium during the process, the medium is circulated through the system by using suitable means. This facilitates maximum irradiation of the catalyst simultaneously allowing the catalyst particles to contact the interface with the target material. A circulating pump (3) is used for the removal of catalyst via the catalyst recovery system (4) at the end of the process run. The catalyst recovery system (4), typically takes the form of a cyclone separator. The level of catalyst in the system is monitored via the process controller (not shown) and adjusted to the required level. The carrier medium is circulated within the bath (1) during the decontamination/destruction process and may be replaced or replenished from the medium storage unit (7) or via the catalyst recovery system (4). The process controller (not shown) is used to monitor the overall process, including monitoring off-gas production within the off-gas monitor/treatment system (8). The off-gas monitoring system (8) provides the means by which the primary process status is monitored. The destruction of organic elements produces $CO_2$, when no further $CO_2$ production is detected the treatment process may be regarded as complete. The residual $CO_2$ given off is collected by use of an active charcoal filter fitted into the off-gas system (8). Sampling can be facilitated in order to allow for conformity in vitro testing, spectroscopic analysis or the like to take place. Once completion of the process has been confirmed the used carrier medium can be disposed of in a recognised manner and the apparatus may be flushed with fresh medium. The flushing process enables all the areas within the apparatus that may have been contaminated by target material to be cleaned, although the system is inherently self-decontaminating. The carrier medium within treatment chamber (1) is then topped-up prior to next usage and the medium in the holding tank (7) replaced. While the method of the invention may generally be carried out at, or close to, atmospheric pressure, materials may be passed through the apparatus under higher pressure particularly during catalyst recovery and/or cleaning stages.

Access to the treatment chamber (1) for this activity may be provided by a glove box lid arrangement (9). This allows for function (if necessary), dismantling and scrubbing of instruments or equipment to remove stubborn or hidden contaminants. These are subsequently circulated and destroyed in the treatment chamber during the treatment process. Safety interlocks may be employed to minimise any risks to personnel during operation, particularly when introducing target material in to the apparatus. Switching means are provided for deactivating the light source automatically when the bath lid (9) is opened.

Prior cleaning of gross material make take place within the decontamination train, that minimises the volume of material to be decontaminated, and improves throughput.

Figure 2:
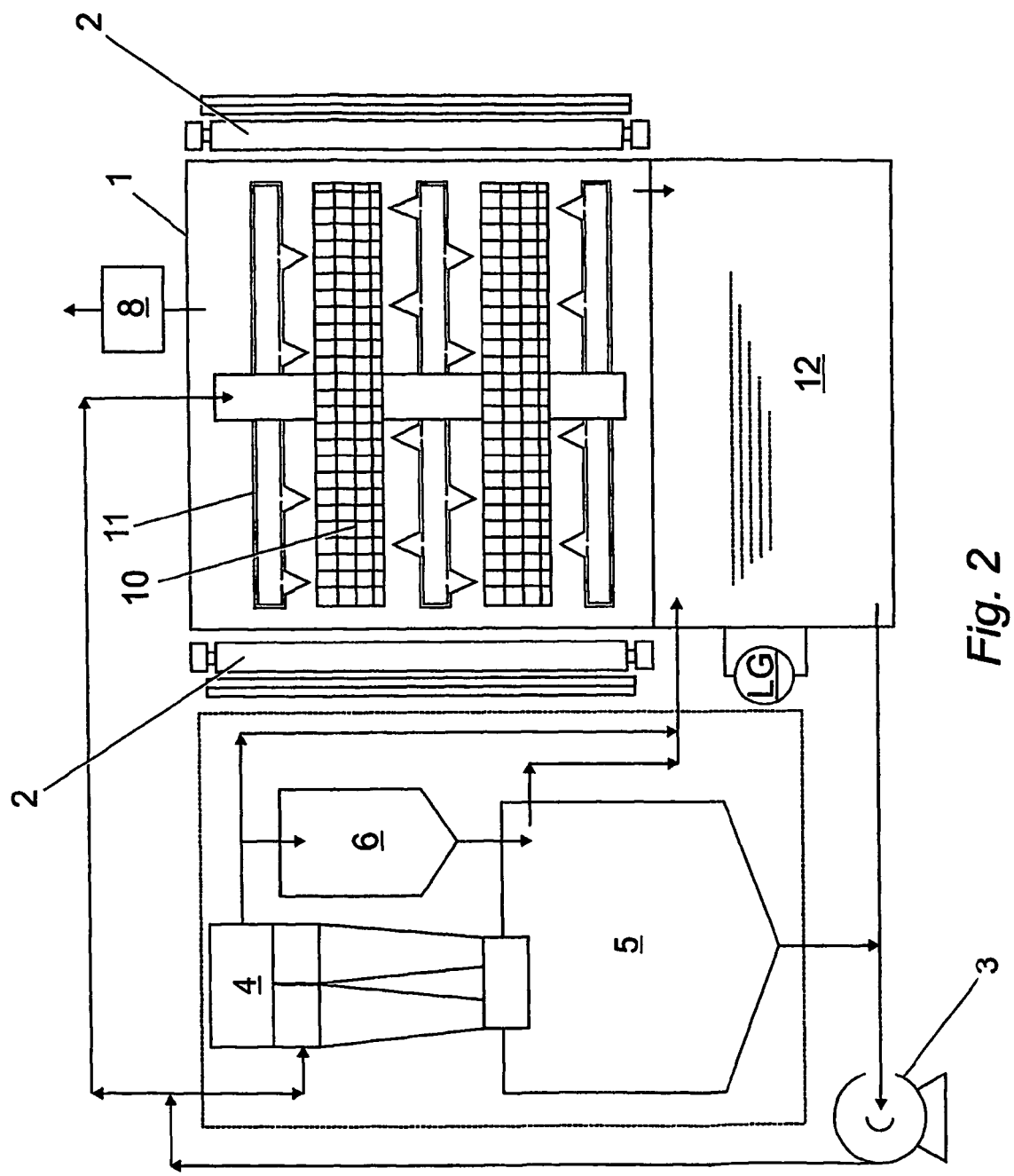
FIG. 2 shows a second embodiment of an apparatus according to the invention.

A second embodiment is shown schematically in FIG. 2. This apparatus is designed for use in hospitals or larger clinics with high throughput of surgical instruments for decontamination. It is designed for operation by dedicated staff with training in the decontamination of surgical instruments and equipment.

The apparatus comprises a treatment chamber (1) having decontamination trays (10) an ultraviolet light source (2) and a medium distribution system (11). Catalyst from the catalyst hopper (6) and/or a catalyst recovery system (4) are introduced into a holding tank (5). The contaminated equipment or product is placed in the decontamination trays (10) and the trays (10) are lowered into the treatment chamber (1). The lid is closed and interlocks engaged before the process is allowed to start. In order to maintain the catalyst in suspension within the medium, the medium is circulated by means of a circulation pump (3) and a medium distribution system (11) having a plurality of rotating spray heads (not shown). The distribution system (11) creates a pressure jet effect that develops a catalyst laden mist or aerosol within the treatment chamber (1) which facilitates optimum contact/interaction between the UV light, catalyst and target material on the contaminated instruments. The carrier medium drains to the bottom of the treatment chamber (1) where it is collected in a circulation header tank (12) which in turn feeds the circulation pump (3). At the end of the treatment process any excess catalyst is recovered from the medium via a catalyst recovery system (4). As described above, a process control (not shown) is provided to monitor progress of the treatment by means of off-gas monitor/treatment system (8). Upon completion of the treatment process, the lid is removed, trays raised and the decontaminated instruments removed.

The medium, including suspended catalyst, may be circulated directly through the treatment chamber (1) from the holding tank (5) during the decontamination process or via the catalyst treatment unit (4) during the catalyst recovery cycle. Carrier medium is sampled for conformity/quality maintenance as described in relation to the previous embodiment. The medium level within the circulation header tank (12) is monitored prior to and during operation and is topped-up as required.

Figure 3:
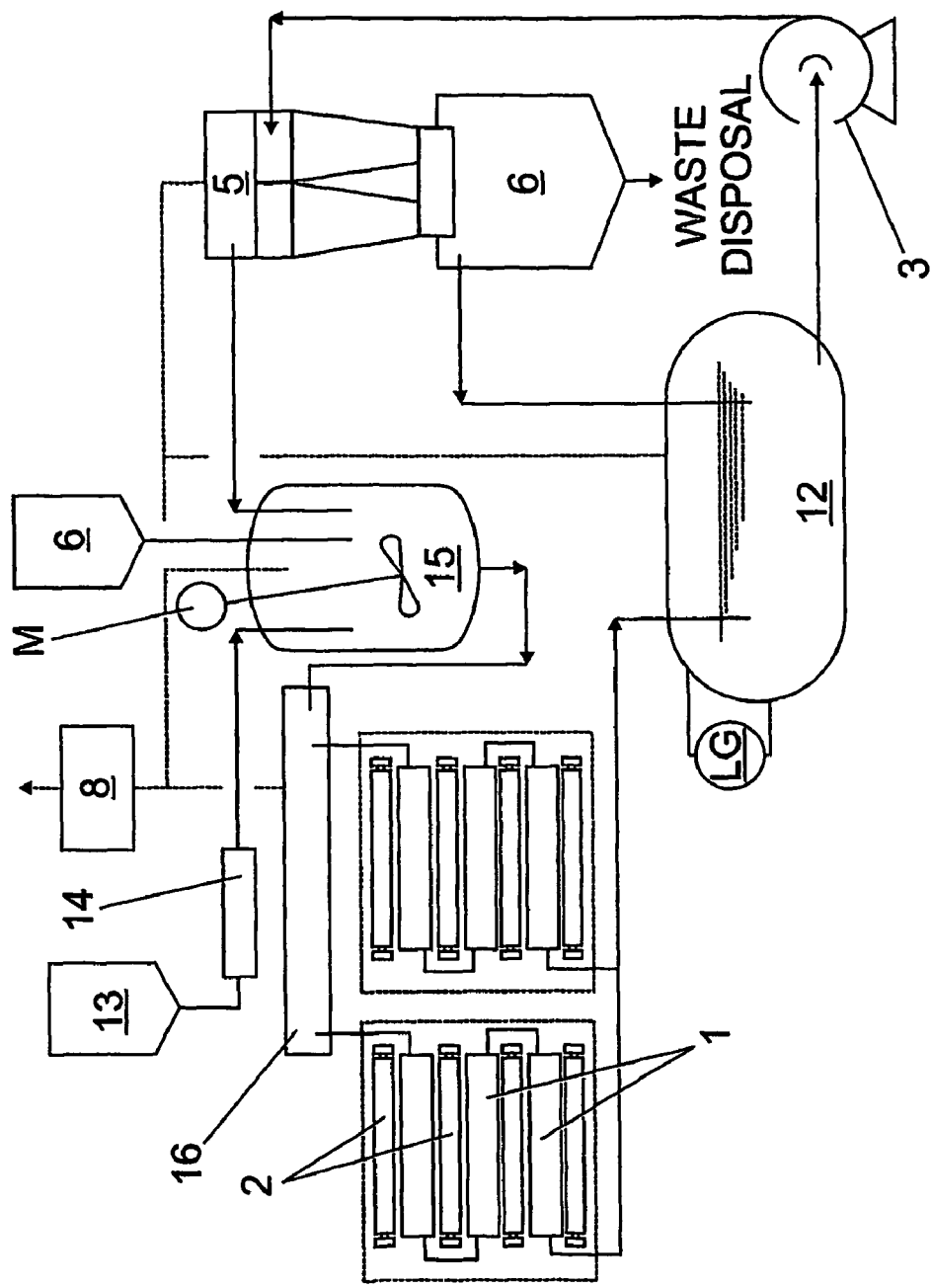
FIG. 3 shows a third embodiment of an apparatus according to the invention.
Figure 4:
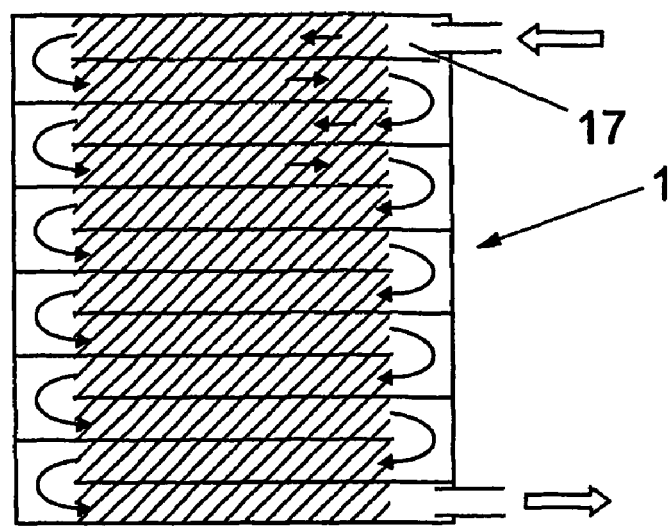
FIGS. 4 and 5 are more detailed views of the treatment chamber of the embodiment shown in FIG. 3.
Figure 5:
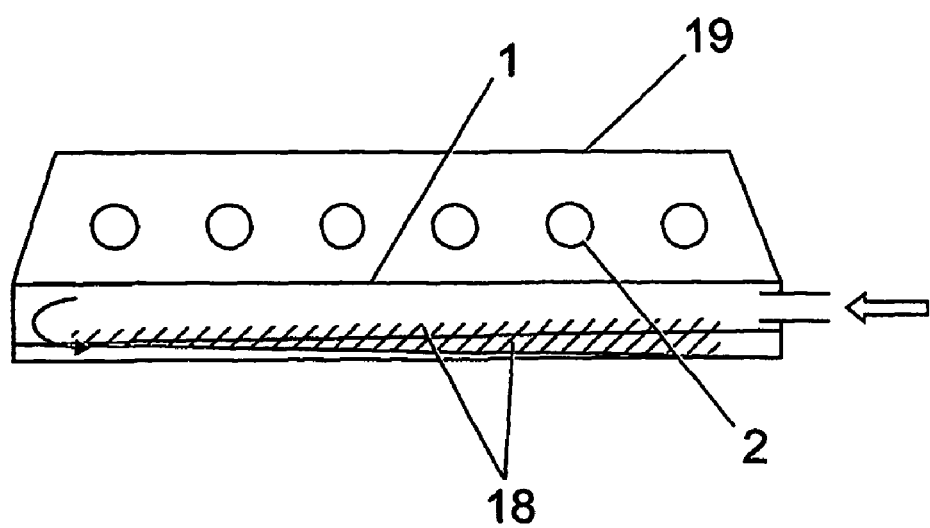

The third embodiment, shown schematically in FIG. 3 with details of the treatment chamber arrangement shown in FIGS. 4 and 5, is designed for either high or low volume destruction of high level bio-hazards such as chemical or biological agent materials, prion contaminated material or the like (and may be adapted to handle solid, liquid or gas phase hazardous materials). It is envisaged that such a system would be operated in a restricted area by dedicated and suitably trained staff.

The apparatus comprises a series treatment chambers (1) the number and configuration of which may be adapted depending upon the nature and quantity of material to be treated. The target material in a suitable pre-prepared state is introduced from a target material hopper (13) under control of metering means (14) into a mixing vessel (15). The carrier medium is fed in to the mixing vessel (15) from the circulation header tank (12) by the circulation pump (3) and catalyst is added from a catalyst hopper (6). The pre-treatment preparation of the target material may include but need not be limited to the breaking down of solids into smaller particles, the suspension of solid particles in a liquid or the absorption of a gas into a liquid. The target material, medium and catalyst mixture cascades into distribution header (16) from which it enters the treatment chambers (1). This method of controlling the flow of the mixture removes any potential pressure other than the hydrostatic head determined by the relationship between the mixing vessel (15) and the distribution header (16). Each treatment chamber (1) comprises a housing that contains a series of tray-like treatment beds and a light source (2). The treatments beds are designed to maximise the time which the carrier medium, catalyst and target material mixture is exposed to the UV light, as well as promoting the formation of turbulent flow. Typically each treatment bed comprises of a series of channels (17) running back and forth across the bed, each channel (17) containing a textured surface (18) designed to induce turbulent flow within the mixture. Control of the flow in this manner prevents the catalyst and target material from being shielded (as could occur in a laminar flow situation) and maximises irradiation effectiveness. The treatment beds are configured with a light source (2), optionally shrouded with a mirror, directly overhead. Each treatment bed further comprises a transparent top plate, typically made from quartz or some other material having suitable light transmission characteristics. The treatment mixture is circulated around the system until the process has been completed or for a suitable duration as dictated by the operator. Any suspended solids, catalyst and other waste products are removed via a catalyst/waste treatment system (4) for storage prior to final disposal.

Specific modifications may be introduced into the carrier medium composition and flow control in order to create the necessary environment for the target material to be suspended within the medium. For example, rotary, ultrasonic or other stirring/agitation means make be incorporated into the apparatus.

The process is controlled using a suitable process monitoring and control system. This includes monitoring the off-gas status by means of an off-gas monitoring/treatment system (8). The off-gas monitoring/treatment system (8) also provides a means for the monitoring and collection/treatment of gaseous reaction products such $CO_2$, $NO_x$, $SO_x$ and the like. In order to treat these off-gases specific equipment such as scrubbers and absorbers may be provided. As before suitable analytical techniques can be employed to monitor the course of the treatment and the content of used waste products and used carrier medium.

The invention is not limited to the embodiments herein described which can be varied in construction and detail.

The invention claimed is:

1. Apparatus for the treatment of hazardous material and decontamination of items contaminated with such material comprising
   an operator accessible treatment vessel having at least one decontamination tray adapted to hold said hazardous material or contaminated items,
   a holding tank capable of holding a carrier medium,
   a catalyst hopper capable of holding a catalyst,
   a mixing vessel connected to each of the holding tank, catalyst hopper and treatment vessel, facilitating mixing of the carrier medium and the catalyst,
   wherein the apparatus comprises one or more treatment chambers, the treatment chambers comprising
   (i) a housing containing a plurality of treatment beds and a light source capable of irradiating contents within the treatment chambers with a predetermined wavelength of light, each treatment bed comprising means for inducing turbulent flow within the carrier medium, and
   (ii) a distribution header connected to the mixing vessel for controlling the flow of carrier medium and catalyst into the treatment chambers.

2. Apparatus according to claim 1 wherein the turbulent flow within the carrier medium is induced by one or more channels on the surface of the treatment bed, each channel having a textured surface.

3. A method for the treatment of hazardous material and decontamination of items contaminated with such material, comprising the steps of providing the hazardous material and contaminated items in a treatment chamber of the apparatus according to claim 1; and irradiating said hazardous material and contaminated items in the presence of a catalyst with light having a wavelength in the range of from 310 to 400 nanometers.

4. A method according to claim 3 comprising the step of treating at least one of equipment and instruments contaminated with hazardous material.

5. A method according to claim 4 comprising maintaining the at least one of equipment and instruments contaminated with hazardous material stationary whilst irradiating it with a predetermined wavelength of light.

* * * * *